United States Patent
Crawford (10) Patent No.: US 7,142,926 B2
(45) Date of Patent: Nov. 28, 2006

(54) QUICK CONNECT EARHOOK SYSTEM FOR BTE DEVICES

(75) Inventor: Scott A Crawford, Castaic, CA (US)

(73) Assignee: Advanced Bionics Corporation, Valencia, CA (US)

(*) Notice: Subject to any disclaimer, the term of this patent is extended or adjusted under 35 U.S.C. 154(b) by 516 days.

(21) Appl. No.: 10/651,651

(22) Filed: Aug. 29, 2003

(65) Prior Publication Data

US 2004/0044389 A1    Mar. 4, 2004

Related U.S. Application Data (60) Provisional application No. 60/407,258, filed on Aug. 30, 2002.

(51) Int. Cl.
*A61N 1/08* (2006.01)
(52) U.S. Cl. .......................... 607/55; 607/57
(58) Field of Classification Search .................. 607/30, 607/31; 439/372, 378, 620; 285/39; 381/330; 338/21; D13/133, 146
See application file for complete search history.

(56) References Cited

U.S. PATENT DOCUMENTS

| | | | | |
|---|---|---|---|---|
| 5,423,692 A | * | 6/1995 | Francis | 439/335 |
| 5,509,750 A | * | 4/1996 | Boike | 403/164 |
| 5,685,730 A | * | 11/1997 | Cameron et al. | 439/335 |
| 5,713,765 A | * | 2/1998 | Nugent | 439/700 |
| 5,824,022 A | | 10/1998 | Zilberman et al. | |
| 5,927,761 A | * | 7/1999 | Bartholomew | 285/114 |
| 5,938,465 A | * | 8/1999 | Fox, Sr. | 439/350 |
| 6,062,910 A | * | 5/2000 | Braquet et al. | 439/620 |
| 6,748,094 B1 | | 6/2004 | Tziviskos et al. | |
| 6,775,389 B1 | * | 8/2004 | Harrison et al. | 381/330 |
| 7,003,876 B1 | * | 2/2006 | Crawford et al. | 29/859 |
| 2003/0031336 A1 | * | 2/2003 | Harrison et al. | 381/330 |
| 2004/0114776 A1 | * | 6/2004 | Crawford et al. | 381/330 |

* cited by examiner

Primary Examiner—Robert E. Pezzuto
Assistant Examiner—Brian T. Gedeon
(74) Attorney, Agent, or Firm—Philip H. Lee; Victoria A. Poissant (57) ABSTRACT

A quick-connect system for mechanically and electrically connecting two components therebetween. In an exemplary embodiment, the mechanical quick-connect is comprised of: a receptacle in the first component; a barrel protruding from the second component; and a lock for locking the barrel inside the receptacle. Electrical connection, such as a coaxial connection, can also be obtained between the barrel and receptacle, while in the locked position by using a pin assembly axially located in the barrel. The lock may comprise a tooth and slot configuration, wherein the tooth is in compressive contact with a spring which compression continuously exerts force on the tooth and causes the end of the tooth to engage to the cam slot on the barrel, thereby locking the barrel inside the receptacle. The barrel may be disengaged with a turn that is less than 180 degrees.

13 Claims, 5 Drawing Sheets

QUICK CONNECT EARHOOK SYSTEM FOR BTE DEVICES

The present application claims the benefit of U.S. Provisional Application Ser. No. 60/407,258, filed Aug. 30, 2002, which application is herein incorporated by reference in its entirety.

BACKGROUND OF THE INVENTION

The present invention relates to electrical and mechanical connector systems that connect two components together and, more particularly, a connector system for mechanically and electrically connecting an earhook to a behind-the-ear (BTE) hearing device. The connector system of the present invention is useful for both conventional, BTE hearing aids and for cochlear stimulation systems employing BTE speech processors.

Implantable cochlear stimulation (ICS) systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by a Wearable Signal Receiver and Processor (WP), converted to a pulse sequence having varying pulse widths and amplitudes and transmitted to an implanted receiver circuit of the ICS system. The implanted receiver circuit is connected to an implantable electrode array that has been inserted into the cochlea of the inner ear. The electrical stimulation current generated by the ICS is applied to varying electrode combinations to create a perception of sound.

A representative ICS system is provided in U.S. Pat. No. 5,824,022, issued Oct. 20, 1998, for "Cochlear Stimulation System Employing Behind-The-Ear (BTE) Speech Processor With Remote Control." The '022 patent is incorporated herein by reference.

The presently available external devices commonly include an earhook attached to the BTE. The earhook is conventionally attached to the BTE hearing device using a threaded interface and requires the user to screw and unscrew the earhook from the BTE device. This procedure can be cumbersome and time-consuming. In addition, when two earhooks are interchangeably used, attaching and detaching the earhook is even more difficult if a cable is attached to the earhook.

Thus, there is a need for an improved connection system for connecting the earhook to the BTE that is simple to operate and more convenient to the user.

SUMMARY OF THE INVENTION

In accordance with one aspect of the present invention, there is provided a quick-connect, mechanical connector system which can provide physical attachment of two device components.

The quick-connect system can comprise: a receptacle, a barrel connector which is dimensioned to fit inside the receptacle, and a lock for locking the barrel inside the receptacle. The lock is configured to engage the barrel connector to the receptacle by inserting the barrel into the receptacle. The lock is configured to disengage the barrel connector from the receptacle by rotationally twisting the barrel by less than 180° and withdrawing the barrel from the receptacle.

In particular, the lock comprises a convexly surfaced cam slot recessed onto the end of the barrel, which cam slot can engage a spring-loaded tooth that fits into the cam slot. The spring-loaded tooth is at least partially contained in a spring retaining chamber that is attached to a side wall of the receptacle. The spring-loaded tooth and spring retaining chamber are located on the receptacle wall to permit the spring-loaded tooth to engage the cam slot after the barrel is inserted into the receptacle. Twisting the barrel within the receptacle disengages the tooth from the cam slot and onto a cylindrical, non-recessed portion of the barrel, whereupon the barrel may be withdrawn from the receptacle. Preferably, the convex cam slot is sized and dimensioned on the barrel so that rotationally twisting the barrel by less than a 90° turn releases the lock.

Thus, as a feature of the invention, the quick-connect system permits a mechanical connection between two components. Such a mechanical only quick connect may be used, for example, to connect a conventional earhook to the body of a BTE device.

In another aspect of the invention, the quick connect may be used to provide both mechanical and electrical connection between two components. This may be accomplished by using the same basic parts as the above described embodiment. However, to achieve a coaxial electrical connection, a pin assembly is also included within the barrel. A spring-loaded, pin contact assembly is placed axially within the barrel such that an end contact for electrical contact is on one end of the pin contact assembly and a depressible, spring-loaded contact pin is located on the other end of the pin assembly. The spring-loaded contact pin contacts a receptacle contact pin for electrical connection. In addition, the tooth in the receptacle provides electrical contact with the barrel to complete an electrical pathway between the receptacle and the barrel connector. A coaxial electrical connection is thereby achieved.

The quick connect system with the coaxial electrical connection is particularly useful to connect a "special" earhook and a BTE body. Unlike a conventional earhook, the special earhook may have electrical devices incorporated therein. For example, a special earhook may have incorporated such electrical devices as a telecoil, a microphone, an FM receiver or an input plug. Such special earhooks may need to be swapped quickly and the quick connect of the present system facilitates this requirement, in addition to providing a coaxial electrical connection.

In another aspect of the invention, a method is provided for electrically and mechanically attaching a first component with a second component. The method comprises providing a contact pin on a barrel receptacle, a pin contact assembly having a spring-loaded, pin contact and an end contact; inserting a barrel into the barrel receptacle; and locking the barrel into the barrel receptacle by employing a tooth which fits into a cammed slot. Electrical contact is made between the tooth and barrel, which are made from conductive material. Electrical contact is also made between the spring-loaded, contact pin and the receptacle contact pin, thereby providing a coaxial electrical connection.

It is thus a feature of the present invention to provide a mechanical and coaxial, electrical connection system that does not require multiple turns to attach or detach two components. The mechanical and electrical connections between two components may be between an earhook and a BTE body. Advantageously, the quick-connect makes attaching an earhook to a BTE body less time-consuming and much more user friendly than a multi-turn threaded connecting system presently available.

It is another feature of the present invention that the connection design easily permits an extension or wire to be placed on an earhook without tangling, since multiple turns are not required.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Behind-the-ear ("BTE") devices refer generally to any hearing device that is placed behind the ears. This includes both hearing aids which merely amplify sound and also more complex, implantable cochlear stimulators (ICS) which have both an external BTE device and an implantable component for directly stimulating cochlear nerves to create a perception of sound.

BTEs used in hearing aids and cochlear stimulators are commonly modular. For example, the BTE may consist of separable components such as the BTE body, a battery portion which attaches to the BTE body and an earhook which can attach to the BTE body. Such modularity is desirable for a number of reasons. The ability to change the size and shape of the earhook accommodates the natural variability in ear shapes and sizes. The detachable battery is preferably modular because batteries become depleted and must be changed periodically. Were the battery integrated into the BTE body, that would require opening the BTE body to access the battery—a task that would not be user friendly.

The quick-connect system of the present invention can provide both a mechanical attachment and coaxial, electrical connection for BTE hearing devices.

Figure 1A:
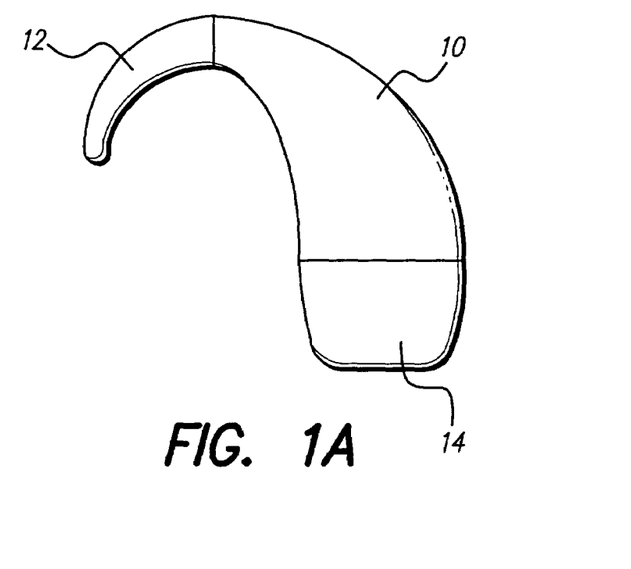
FIG. 1A depicts a complete behind-the-ear (BTE) hearing device with an earhook attached.

FIG. 1A shows a modular BTE body 10, a standard earhook 12, and a detachable battery compartment 14. The earhook 12 is curved and BTE body 10 continues this curve. The earhook 12 is placed over the top and front of the ear, while the BTE body 10 and battery compartment 14 hangs behind the ear. Various batteries of different sizes may be interchangeably attached to the BTE device 10 depending upon the needs of a user. A more detailed description of a BTE device is found in U.S. Pat. No. 5,824,022, previously incorporated by reference.

Figure 1B:
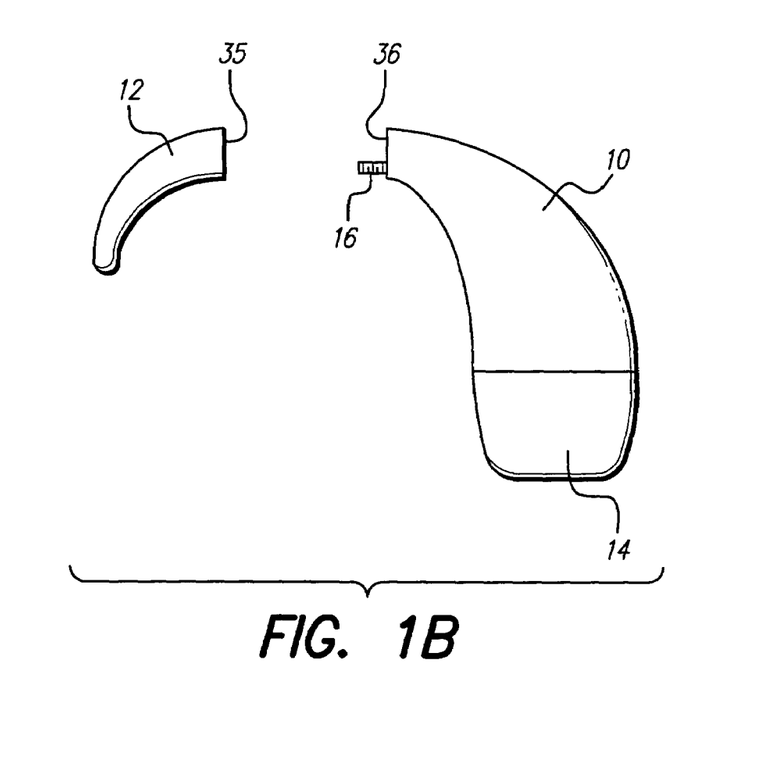
FIG. 1B shows another illustration of the BTE device with the earhook portion detached from the BTE.
Figures 2A, 2B:
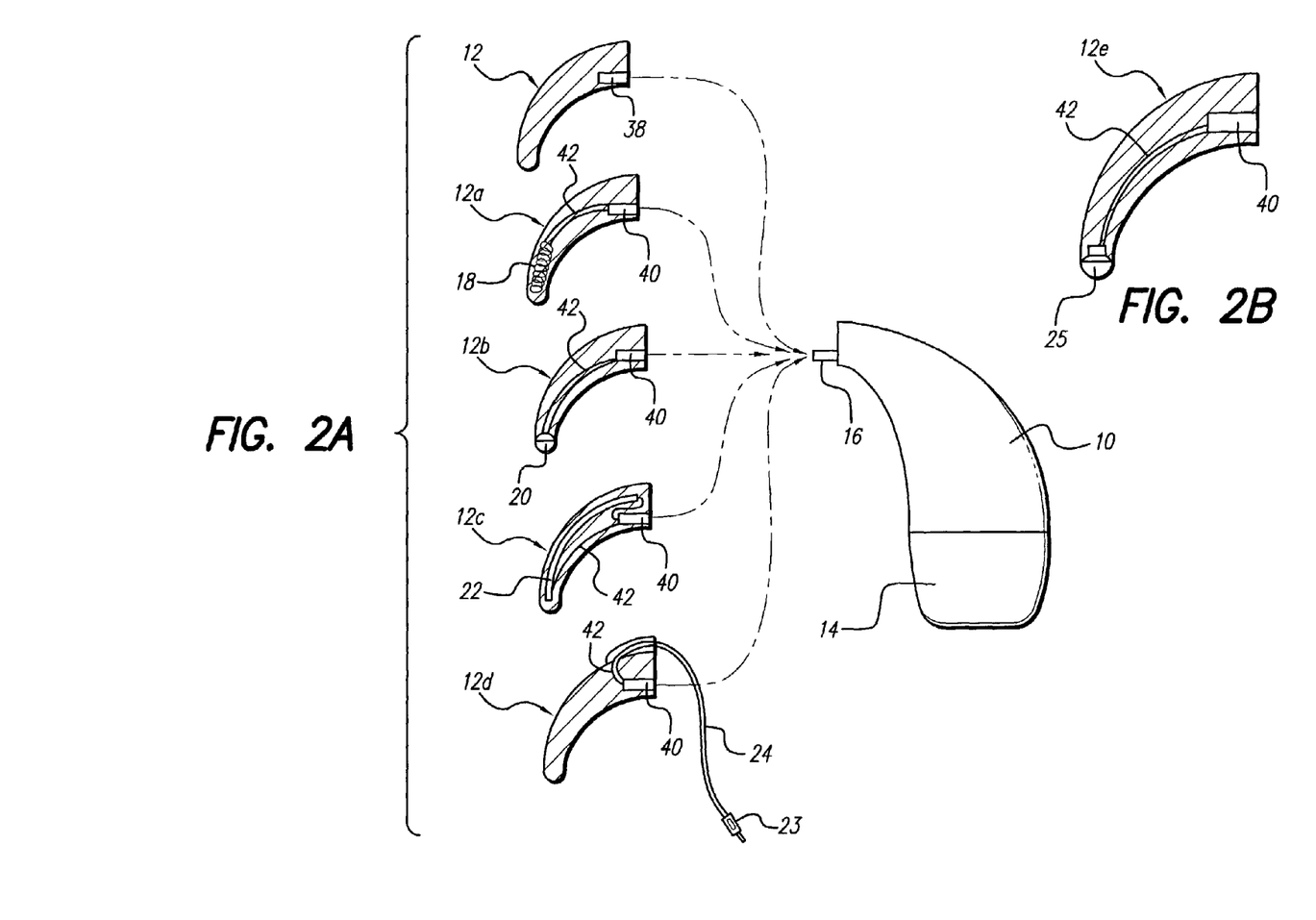
FIG. 2A shows cross-sectional views of a standard earhook and four special earhooks, which earhooks can be interchangeably attached to the BTE device.
FIG. 2B shows a cross-sectional view of a special earhook for use with a conventional BTE, or other hearing aid device, that positions a speaker in proximity to the ear canal.

FIG. 1B, shows an illustration of the earhook 12 detached from the BTE body 10. Standard earhooks do not contain within them any electronics or devices and thus no electrical connection is needed between such an earhook 12 and BTE body 10. Hence, with a standard earhook, connector 16 functions merely to mechanically connect the two components together. A conventional mechanical connection such as a multi-turn screw 16 can be employed. An earhook 12 is attached by aligning it relative to the BTE screw 16, as shown in FIG. 1B, and rotating the earhook 12 multiple turns to allow entry of screw 16 into the complementary threaded receptacle 38 as shown in FIG. 2A (top figure). Surfaces 35 and 36 can provide a friction fit to resist movement between the earhook and the BTE body 10.

As BTE hearing devices have become more sophisticated, however, the earhook 12 is now being increasingly used to contain electrical devices and hence, in those instances, an electrical communication means is necessary between the earhook 12 and the BTE body 10. These earhooks, having electrical devices are referred to, herein, as "special earhooks." U.S. patent application Ser. No. 09/785,629, filed Feb. 16, 2001, discloses a number of devices that may be placed into the special earhook of a BTE device. This application is herein incorporated by reference.

FIGS. 2A and 2B summarize the devices disclosed as special earhooks in the '629 patent application. FIG. 2A shows these devices in the special earhooks 12a through 12e: a telecoil 18 embedded in the earhook; a microphone 20; an FM receiver 22; and an extension cable 24 that terminates in an input plug 23. Lead conductor 42 electrically couples the devices to the mechanical and electrical connector receptacle 40.

FIG. 2B shows a speaker 25 adapted for use with conventional hearing aids. Conventional hearing aids utilize a speaker in the body of the hearing aid and a passage through an earhook to carry the sound into the user's ear. Conventionally, the microphone of the hearing aid is also located in the hearing aid body. Because both the microphone and speaker are physically close to each other, some acoustic coupling (feedback) can occur between the microphone and the receiver, thus degrading performance. The special earhook 12e, however, positions the hearing aid speaker 25 near the tip of the earhook and, thus, closer to the user's ear, but more distant from the microphone. Lead conductor 42 or conductors carry the signal from the connector 40 to the speaker 25.

Connector 38 is merely a threaded mechanical receptacle, without any electrical connection, since earhook 12 does not have any electrical device incorporated. However, special earhooks 12a, 12b, 12c, 12d, and 12e all require not only a mechanical connection between the earhook 16 and BTE body 10, but also an electrical connection to the various electrical devices located in the special earhooks. In accordance with the present invention, a method of providing this electrical communication is to use a special connector system 40 and 16 to double not only as a mechanical connector, but also as a coaxial connector. Advantageously, such a dual function connector eliminates the need to provide a separate electrical connector for connecting the devices in the earhook to the BTE body 10.

The coaxial connector system 16 and 40 may use the same thread size and pitch as used in standard earhooks, thus allowing the use of standard earhooks with the BTE device. As shown in FIG. 1B, the earhook interface surface 35 and a BTE interface surface 36 can provide a friction fit between the earhook 12 and BTE device 10 as the earhook 12 is screwed onto the coaxial connector 16. However, while a coaxial connection is provided, any connection system that uses threads which requires multiple turns is not user friendly. Such a connection procedure is not only time consuming, but with some special earhooks such as 12d which has an extension cord 24, it can be problematic since the cord can become easily tangled.

The present invention provides a quick-connect system which makes detaching the special, as well as standard earhooks, faster and easier and does not require rotating the earhook multiple times.

FIGS. 3, 3A, 3B, 3C, 3D, 4, 4A, and 5 illustrate the quick-connect system, in accordance with the present invention.

Figure 5:
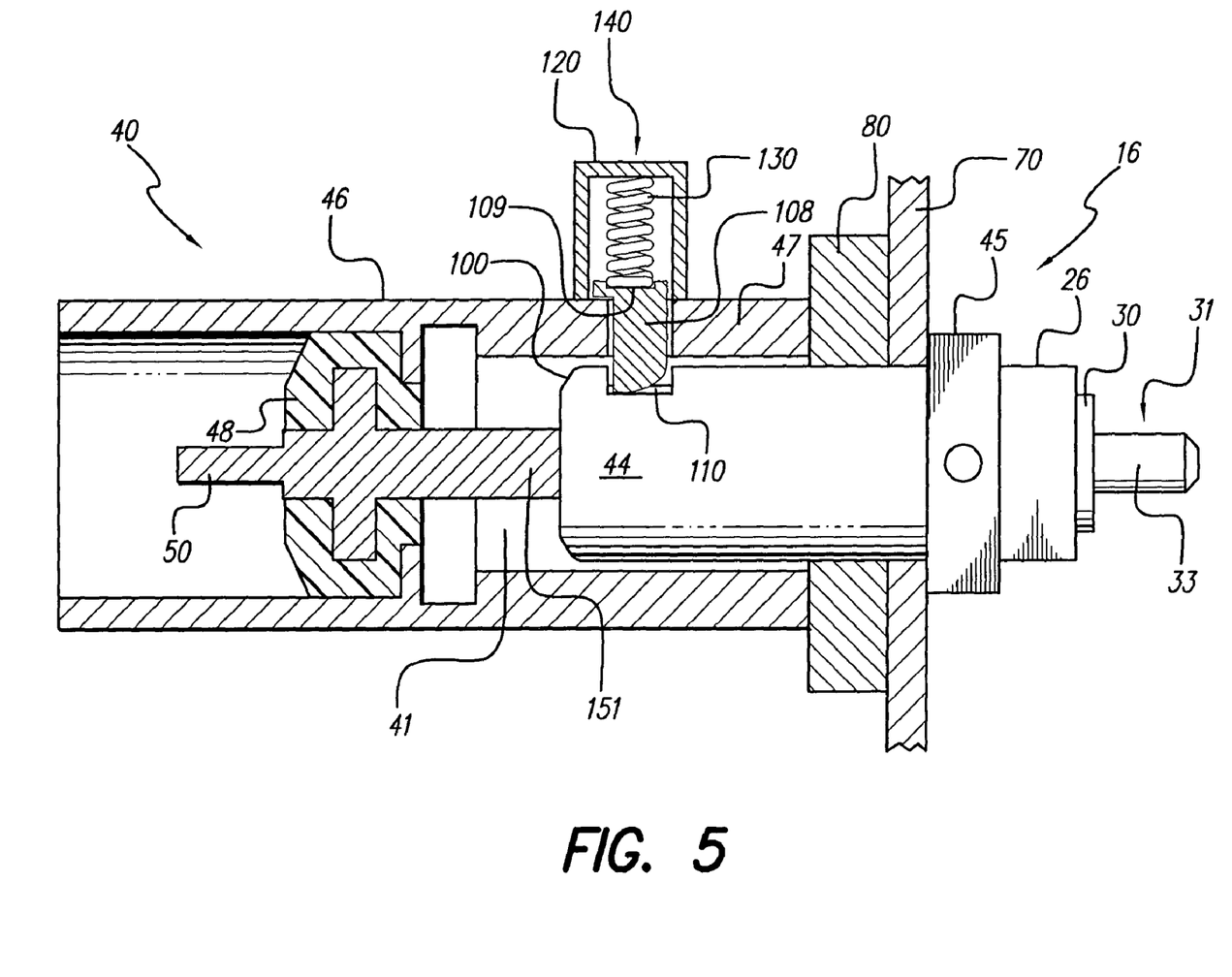
FIG. 5 shows a view of the connection system of the present invention which includes a longitudinal, cross-sectional view of a barrel receptacle, a side view of the barrel inside the barrel receptacle and a lock which is comprised of a spring-loaded tooth recessed into a cammed slot located on the barrel.

FIG. 5 shows a view of the complete quick-connect system, in accordance with the present invention, which system provides both mechanical and electrical connections between two components, such as an earhook and an BTE body. The mixed illustration show a cross-sectional side view of the barrel receptacle 40 and a side view of the barrel connector 16 with the inserted barrel 44.

Figure 3:
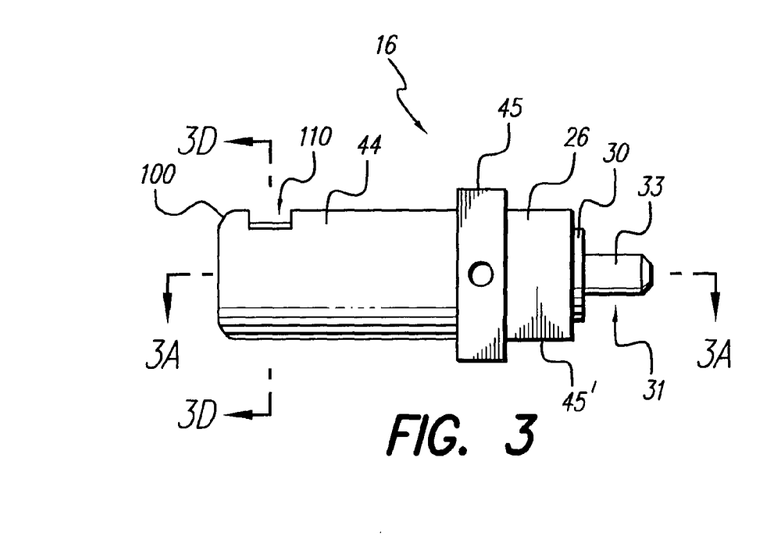
FIG. 3 shows, in accordance with the present invention, a side view of a barrel connector of the quick-connect system.

FIG. 3 shows the coaxial, barrel connector 16 which is mounted in the BTE device 10 such that the barrel 44 extends from interface surface 36 (as shown in FIG. 1B) of BTE body 10. A square shoulder or flange 45 at the posterior end of the barrel 44 facilitates mounting the barrel connector 16 inside the BTE so that the square shoulder 45 is, in one embodiment, flush with the inside BTE wall surface 36. Advantageously, using a square shoulder 45 provides a means to rotationally index the coaxial connector 16 relative to the BTE device 10. The shape of the square shoulder 45 prevents rotational movement inside the BTE once the coaxial connector is mounted.

Figure 3A:
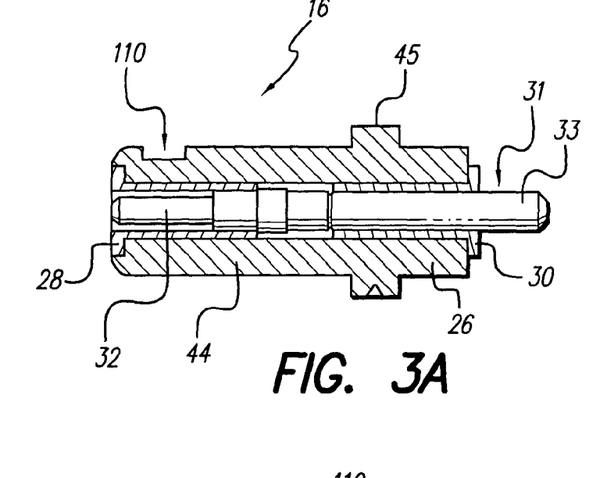
FIG. 3A shows, in accordance with the present invention, a cross-sectional view of the barrel connector and pin contact assembly axially placed in the barrel connector, the view taken along line 3A—3A of FIG. 3.

FIG. 3A shows a cross-sectional view of the barrel connector 16, taken along line 3A—3A of FIG. 3 and a view of the pin assembly 31 inside. The round rear 26 of the barrel connector 16 and the barrel 44 are preferably made of bronze, but may be constructed from other conductive material with mechanical strength and characteristics suitable for use as an electrical connector. A convex, cam slot 110 is cut into the anterior end of the barrel 44. The exterior surface of the pin assembly 31 can have a diameter of about 0.034 inches and be supported by insulative bushings 28 and 30. The bushing 30 can be attached to the contact end 33 with adhesive to fix the pin assembly 31 to the barrel connector 16. A spring-loaded contact pin 32 can be depressed into the pin assembly 31.

The pin assembly 31 protrudes at the posterior end at end contact 33, providing one electrical contact to electronic circuitry in the BTE body 10. For a coaxial electrical connection, the electronic circuitry in the BTE body can also electrically connect to cylindrical end (or "rear") 26 of the barrel connector 16.

Figure 3B:
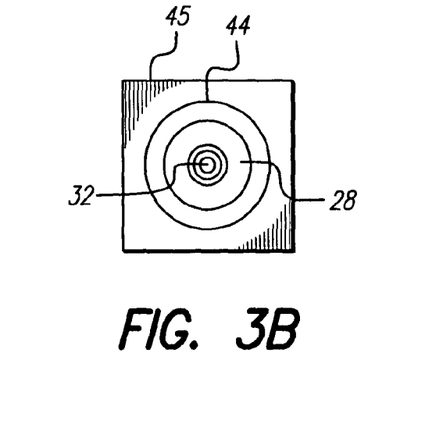
FIG. 3B shows a front view of the barrel connector of FIG. 3.

FIG. 3B shows a front view of the barrel connector 16. The square shoulder or flange 45 allows the coaxial connector to be accurately positioned rotationally within the BTE device 10 and then fixed into place to thereby provide counter-rotational resistance.

Figures 3C, 3D:
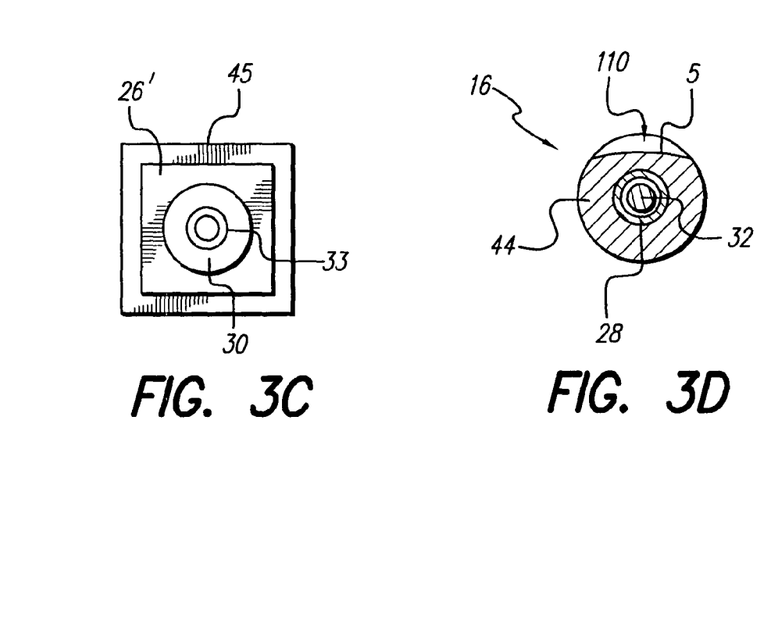
FIG. 3C shows a rear view of the barrel connector of FIG. 3.
FIG. 3D shows a cross-sectional view of the barrel and cam slot taken along line 3D—3D of FIG. 3.

FIG. 3C shows a rear view of the barrel connector 16. In this embodiment the rear 26' of the barrel connector 16 can be shaped as a small, square, instead of a circle. The square shape can be advantageous for anchoring the barrel connector to a BTE device.

FIG. 3D shows a cross-sectional view of the barrel connector 16 taken at line 3D—3D of FIG. 3. It can be seen that the cam slot 110 has a convex surface curvature 5 and is recessed in barrel 44.

Figure 4:
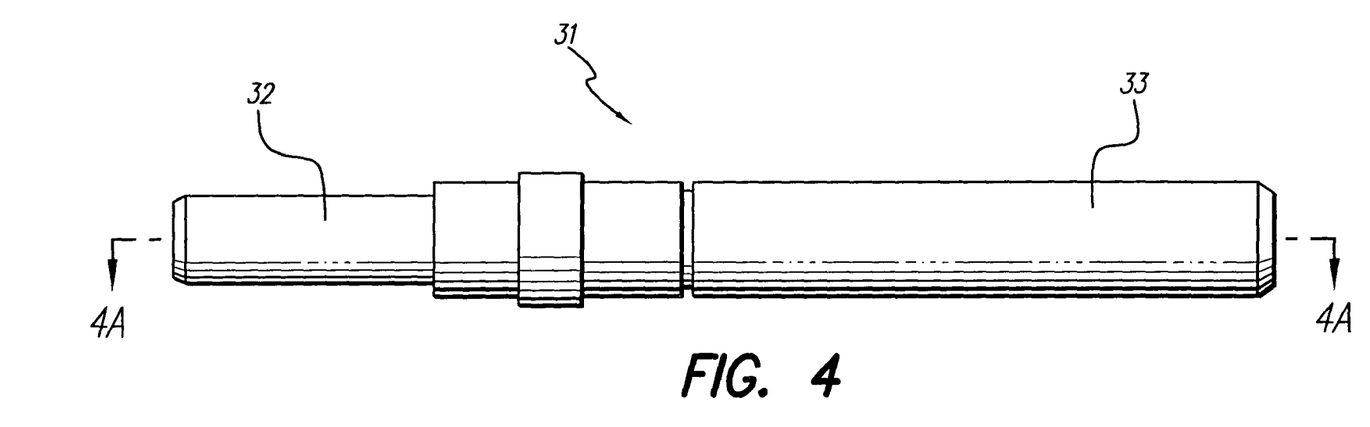
FIG. 4 shows a side view of the pin contact assembly.

FIG. 4 shows another view of the pin contact assembly 31 alone. The spring-loaded contact pin 32 protrudes out from pin assembly 31 and is depressible into the pin assembly. The contact end 33 is used to electrically connect to the BTE electronics.

Figure 4A:
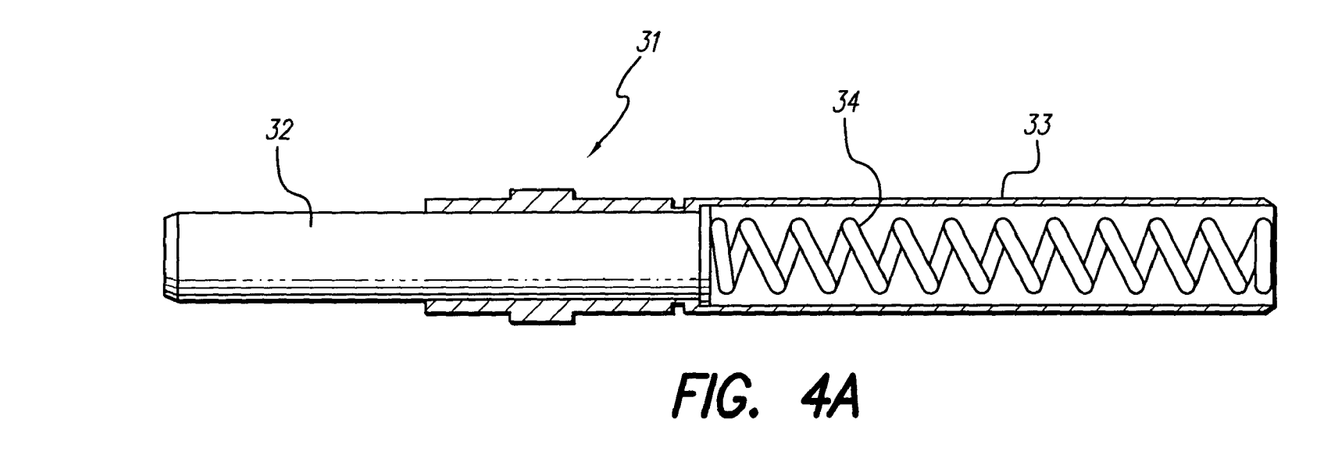
FIG. 4A shows a cross-sectional view of the pin contact assembly shown in FIG. 4, taken along line 4A—4A of FIG. 4.

FIG. 4A shows a longitudinal, sectional view of the pin assembly 31 taken along line 4A—4A of FIG. 4. The spring 34 is shown pushing the spring-loaded contact pin 32 outwardly from the open end of the outer shell of the contact pin 33. Both the spring-loaded, contact pin 32 and the contact end 33 are hollow to permit a pin assembly spring 34 to be housed within the contact pin 32 and contact end 33.

FIG. 5 shows the component parts of the complete quick-connect system of the present invention. To summarize, the main components of the system include: (a) a barrel connector 16 having a barrel 44 (b) a barrel receptacle 40 which can receive the barrel 44 and (c) a locking latch 140. The barrel receptacle 40 is incorporated into one device component, such as a special earhook. The barrel connector 44 is incorporated into another component such as the BTE body 10 at the surface 36.

The barrel 44 is substantially a cylinder having preferably a rounded anterior end 100 that can be inserted into the correspondingly barrel-shaped receptacle chamber 41. The barrel connector 44 also includes a square stop (or flange) 45 that encircles and divides barrel 44 from the posterior (rear) cylindrical portion 26. The square stop or flange 45 can abut against the wall of the BTE housing 70 and can be fixed to the BTE housing by various known means such as mechanical fixation or adhesives. Alternatively, the square stop may be inserted partly into the wall 70.

The opening of the barrel receptacle 40 may have an elastomeric O-ring 80 which is attached to and abuts the opening end of receptacle chamber 41. When barrel 44 is fully inserted into the barrel receptacle 40, the elastomeric O-ring 80 provides both a compression fit and friction fit with the BTE housing 70 and thereby resists turning and, further, allows the earhook 12 to be positioned over a small range of rotational positions relative to the BTE body 10.

The outer surface of the barrel receptacle 40 can be shaped as a cylinder or any other convenient shape. Specifically, the outside surface wall 46 of the barrel receptacle 40 can have ridges, protrusions and other extensions which can help fix the barrel receptacle to the earhook 10, which earhook may be made from a moldable polymer. The barrel receptacle 40 can be made from materials such as metals, ceramics or high density plastics.

The spring retaining enclosure 120 is integrated into one part of the barrel receptacle wall portion 47. This spring retaining enclosure contains a spring 130 which provides a constant, spring-loaded outward pressure on tooth 108. One side of the tooth 108 is designed to retain one end of the spring 130 by having a circular recess 109, wherein one end of the spring 130 is confined. The end of the tooth 108 enters the receptacle chamber 41 of the barrel receptacle 40 through a hole in receptacle wall portion 47. When fully extended outward, the tooth 108 can extend slightly past the inner surface of the chamber wall 47. When barrel 44 is inserted into the receptacle chamber 41, the curved part of the tooth meets the barrel causing the tooth to first retract as the barrel pushes the tooth away, then the tooth snaps into cam slot 110 on the barrel 44, thus locking the barrel into the barrel receptacle and, hence, the BTE body 10 to a special earhook, 12*a–e* (shown in FIGS. 2A and 2B).

Referring again to FIG. 3D, it can be seen that the cam slot 110 on barrel 44 has a convex surface curvature 5 to permit the tooth 108 to slide off the cammed surface as the barrel 44 is axially rotated by about 45° to 90°. By rotating the barrel 44 in either rotational direction by about 45° to 90°, the tooth 108 is pushed back into the spring retaining enclosure 120 and the tooth makes contact with the non-recessed portion of the cylindrical surface of the barrel 44. When this is done, the tooth is no longer in a locked mode and the barrel 44 can then be retracted from the barrel receptacle 46, thereby detaching the barrel from the barrel receptacle, and in the process, detaching the special earhook 12 from the BTE body 10.

Locking the barrel 44 into the receptacle chamber 41 not only establishes a mechanical connection between the barrel and barrel receptacle, but also can establish an electrical connection, such as for instance, a coaxial connection. The quick-connect system of the present invention, as explained previously, is especially suited for use with special earhooks, such as depicted in 12*a–e* in FIGS. 2A and 2B. Such special earhooks often require that they be quickly detached and immediately replaced by another special earhook. In addition, some special earhooks may have dangling wires which make the conventional mode of attachment, i.e., multiple turns with screws and threaded receptacles, too time consuming and awkward.

Referring once again to FIG. 5, a first electrical connection is provided through receptacle contact pin 151 which contacts the spring-loaded pin contact 32 (as shown in FIG. 3A), and a second electrical connection is provided when tooth 108 contacts barrel 44. Wall 46, barrel 44 and rear 26 of barrel connector 16 are therefore in electrical contact providing the second electrical connection. The bushing 48 electrically insulates the barrel receptacle wall 46 from the coaxial contact pin 50 and also provides physical support to the coaxial contact pin 50.

Various alternative embodiments of the barrel connector 16 and the barrel receptacle 40 will be apparent to those skilled in the art and are within the scope of the invention. In particular, in one embodiment of the invention, the quick connect may be used as a mechanical connection or as a mechanical and electrical connection. Thus, as shown in FIG. 2A, if connection 16 is the quick connect of the present invention, having a coaxial electrical connection, it may be connected to special earhooks 12*a* through 12*d* and, furthermore, quick connect 16 may be compatibly connectable to conventional earhook 12, although the electrical connection will be unused.

Alternatively, the quick connect may be made solely as a mechanical quick connect for two components. In such a case, the quick connect must include: a barrel receptacle; a barrel connector, and a lock. No pin assembly is needed. The receptacle is made part of the first component. The barrel connector is dimensioned to fit inside the barrel receptacle and the barrel connector is incorporated as part of the second component. The lock may be a configuration to engage the barrel connector to the receptacle when the barrel is inserted into the receptacle. The lock should also be configured to disengage the barrel connector from the receptacle by rotationally twisting the barrel by less than 180° and withdrawing the barrel from the receptacle. Preferably, the barrel should disengage with a twist of less than about 90° and, more preferably, less than about 45°. An embodiment of a locking system that permits disengagement with about a 45° turn includes a convex surfaced slot recessed into the end of the barrel and a spring-loaded tooth, dimensioned to fit into the cam slot, as previously described.

In another aspect of the invention, a method is provided for electrically and mechanically attaching a first component with a second component. The method comprises: providing a contact pin on a barrel receptacle, and providing a pin contact assembly having a spring-loaded, pin contact and an end contact; inserting a barrel into the barrel receptacle; and locking the barrel into the barrel receptacle by employing a tooth which fits into a cammed slot. Electrical contact is made between the tooth and barrel, which are made from conductive material. Electrical contact is also made between the spring-loaded, contact pin and the receptacle contact pin, thereby providing a coaxial electrical connection.

Thus, in summary, the present invention is a connector system and method for attaching both a standard earhook and special earhooks to a BTE body. The special earhooks, which provide a variety of functions can be conveniently and quickly attached and detached to a BTE device.

Although the quick-connect of the present invention has been described in the context of its application to a BTE device, it will be appreciated that a coaxial quick-connect system, in accordance with the present invention, also has utility to any application where two components must be quickly and easily attached and detached. The quick-connect of the present invention may be used as a purely mechanical connection system or as a system that provides, simultaneously, both mechanical and electrical connections. These other applications are intended to come within the scope of the present invention.

While the invention herein disclosed has been described by means of specific embodiments and applications thereof, numerous modifications and variations could be made thereto by those skilled in the art without departing from the scope of the invention set forth in the claims.

What is claimed is:

1. A quick-connect system for mechanically connecting a first component and a second component, wherein the first component and second component are configured to be used with a hearing device the system comprising:
 a receptacle which is part of the first component;
 a barrel connector, which is dimensioned to fit inside said receptacle, said barrel connector is part of the second component; and
 a lock for locking the barrel inside the receptacle, wherein the lock comprises:
  a cam slot on the barrel; and a spring-loaded tooth, dimensioned to fit into the cam slot, wherein the spring-loaded tooth is at least partially contained in a spring retaining chamber, which chamber is attached to a side wall of the receptacle;

wherein the spring-loaded tooth and spring retaining chamber are positioned to permit the spring-loaded tooth to engage the cam slot after the barrel is inserted into the receptacle, and wherein the cam slot is sized and configured so that when the barrel is twisted between about 45° and 90°, the barrel is disengaged from the spring-loaded tooth, allowing the barrel to be withdrawn from the receptacle.

2. The quick connect system of claim 1, wherein the first component is an earhook of a hearing aid and the second component is a hearing aid body.

3. The quick-connect system of claim 2, wherein the second component is a Behind-the-Ear (BTE) of a cochlear implant device.

4. A quick-connect system for both mechanically and electrically connecting a first component and second component, wherein the first component and second are to be used with a hearing device the system comprising:

a receptacle which is part of the first component;

a barrel dimensioned to fit inside said receptacle, said barrel connector is part of the second component;

a lock for locking the barrel inside the receptacle, wherein the lock comprises:

a cam slot located on the barrel; and a spring-loaded tooth, dimensioned to fit into the cam slot, wherein the spring-loaded tooth is at least partially contained in a spring retaining chamber, which chamber is attached to a side wall of the receptacle; and wherein the spring-loaded tooth and spring retaining chamber are positioned to permit the spring-loaded tooth to engage the cam slot after the barrel is inserted into the receptacle, and wherein the cam slot is sized and configured so that when the barrel is twisted by about 90° or less, the barrel is disengaged from the spring-loaded tooth, allowing the barrel to be withdrawn from the receptacle; and an electrical coupling between said receptacle and barrel connector.

5. The quick connect system of claim 4, wherein the first component is an earhook of a hearing aid and the second component is a hearing aid body.

6. The quick-connect system of claim 5, wherein the second component is a BTE of a cochlear implant device.

7. The quick-connect system of claim 4, wherein the electrical coupling is a coaxial connection between the barrel and receptacle.

8. The quick-connect system of claim 7, further comprising:

a pin contact assembly, having a spring-loaded, contact pin on the anterior end and an end contact on the posterior end, wherein the barrel connecter has an axial channel therethrough, and the pin contact assembly is placed inside said channel;

wherein the receptacle includes a receptacle contact pin, insulated from the receptacle wall; and wherein a coaxial connection is made by contacting the barrel wall to the receptacle wall, and contacting the spring-loaded, contact pin to the receptacle contact pin.

9. The quick-connect system of claim 8, wherein the first component is a special earhook and the second component is a BTE of an implantable cochlear stimulator.

10. The quick-connect system of claim 9, wherein the special earhook incorporates a device selected from the group consisting of a telecoil, a microphone, an FM receiver, a speaker and an input plug.

11. A method of electrically and mechanically attaching a first component and a second component wherein the first component and second component are configured to be used with a hearing device comprising:

providing a barrel receptacle, said barrel receptacle is part of the first component, and wherein the barrel receptacle includes a spring retaining chamber that is attached to a side wall of the barrel receptacle;

providing a barrel connector, said barrel connector is part of the second component;

providing a barrel receptacle contact in pin, wherein the barrel receptacle contact pin is part of the barrel receptacle;

providing a pin contact assembly including an end contact and a spring-loaded, pin contact, wherein the pin contact assembly is part of the barrel connector, and wherein the spring-loaded, pin contact, is used to contact the barrel receptacle contact pin;

inserting the barrel connector into the barrel receptacle; and locking the barrel connector into the barrel receptacle by employing a tooth which fits into a cammed slot, said cammed slot is part of the barrel connector, wherein the tooth is spring-loaded, and the end of the tooth enters through a hole in the spring retaining chamber, and the tooth is in a non-axial orientation with the barrel connector;

wherein electrical contact is made between the tooth and barrel connector, said tooth and barrel connector made from conductive material; and wherein electrical contact is made between the spring-loaded, pin contact and the receptacle contact pin, which spring-loaded, pin contact is electrically isolated from the barrel receptacle, thereby providing a coaxial electrical connection.

12. The method of claim 11, wherein the first component is a special earhook and the second component is a BTE body.

13. The method of claim 12, wherein the special earhook incorporates a device selected from the group consisting of a telecoil, a microphone, an FM receiver, and an input plug.

* * * * *